United States Patent
Deane et al.

(10) Patent No.: US 9,517,015 B2
(45) Date of Patent: Dec. 13, 2016

(54) DENTAL APPARATUS AND METHOD OF UTILIZING THE SAME

(71) Applicant: KONINKLIJKE PHILIPS N.V., Eindhoven (NL)

(72) Inventors: Steven Charles Deane, Cambridge (GB); Olaf Thomas Johan Antonie Vermeulen, Oss (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 16 days.

(21) Appl. No.: 14/649,575

(22) PCT Filed: Nov. 14, 2013

(86) PCT No.: PCT/IB2013/060120
§ 371 (c)(1),
(2) Date: Jun. 4, 2015

(87) PCT Pub. No.: WO2014/097008
PCT Pub. Date: Jun. 26, 2014

(65) Prior Publication Data
US 2015/0297089 A1   Oct. 22, 2015

Related U.S. Application Data

(60) Provisional application No. 61/740,797, filed on Dec. 21, 2012.

(51) Int. Cl.
*A61B 5/00* (2006.01)
*A46B 15/00* (2006.01)
*A61C 1/00* (2006.01)

(52) U.S. Cl.
CPC ......... *A61B 5/0088* (2013.01); *A46B 15/0036* (2013.01); *A61B 5/0071* (2013.01);
(Continued)

(58) Field of Classification Search
CPC ................... A46B 15/0036; A61B 2560/0223; A61B 2560/0238; A61B 2576/02; A61B 5/0071; A61B 5/0088; A61B 5/7246; A61B 5/7282; A61C 1/0015
See application file for complete search history.

(56) References Cited

U.S. PATENT DOCUMENTS 5,894,620 A     4/1999  Polaert et al.
6,024,562 A *   2/2000  Hibst ................... A61B 5/0088
                                                433/29

(Continued)

FOREIGN PATENT DOCUMENTS

JP     2010508947 A    3/2010
JP     2012086022 A    5/2012

(Continued)

*Primary Examiner* — Mark R Gaworecki (57) ABSTRACT

A dental apparatus (4) is provided. The dental apparatus includes a handle (6). A controller (20) operably couples to the housing and includes a calibration module (44) configured to calibrate the dental apparatus. The dental apparatus emits a modulated excitation signal and the calibration module compares a detected modulated fluorescence signal with first and second reference values such that if a difference between the detected modulated fluorescence signal and the second reference signal is greater than a difference between the first reference value and the second reference value then the first reference value is updated.

15 Claims, 5 Drawing Sheets

(52) U.S. Cl.
CPC .......... *A61B 5/7246* (2013.01); *A61B 5/7282* (2013.01); *A61C 1/0015* (2013.01); *A61B 2560/0223* (2013.01); *A61B 2560/0238* (2013.01); *A61B 2576/02* (2013.01)

(56) References Cited

U.S. PATENT DOCUMENTS

| | | |
|---|---|---|
| 6,102,704 A | 8/2000 | Eibofner et al. |
| 6,485,300 B1 | 11/2002 | Muller et al. |
| 2005/0255423 A1 | 11/2005 | Hack et al. |
| 2010/0178252 A1 | 7/2010 | Sagel et al. |
| 2011/0318712 A1 | 12/2011 | Reddy et al. |
| 2014/0199651 A1 | 7/2014 | Adachi |

FOREIGN PATENT DOCUMENTS

| | | |
|---|---|---|
| JP | 2013042906 A | 3/2013 |
| JP | 2013531534 A | 8/2013 |

\* cited by examiner

DENTAL APPARATUS AND METHOD OF UTILIZING THE SAME

CROSS-REFERENCE TO PRIOR APPLICATIONS

This application is the U.S. National Phase application under 35 U.S.C. §371 of International Application No. PCT/IB2013/060120, filed on Nov. 14, 2013, which claims the benefit of U.S. Provisional Patent Application No. 61/740,797, filed on Dec. 21, 2012. These applications are hereby incorporated by reference herein.

TECHNICAL FIELD

The present disclosure relates to a dental apparatus and method of utilizing the same. More particularly, the present disclosure relates to a dental apparatus and method of use of the dental apparatus including a modulated excitation signal causing an emitted fluorescence light that is analyzed to detect dental plaque and a calibration module configured to calibrate the dental apparatus for an individual user.

BACKGROUND ART

It is desirable to detect plaque deposits in the oral cavity to direct action for removal, for example by using toothbrushes (manual or power), tooth floss, tooth picks, or oral irrigators, as detection indicates the areas at which dental cleaning effort should be focused. Such deposits can be difficult to detect in situ/in vivo on the teeth, gums, tongue, or cheek. It is especially important to detect dental plaque. For detection of dental plaque it is known to use fluorescence measurement, in which incident radiation is directed at the surfaces of the oral cavity, and fluorescence radiation having characteristics associated with the presence of biological deposits is emitted from the surfaces and is detected.

In the state of the art there are two general methods for detecting dental plaque. One method uses primary fluorescence, where the fluorescence of dental plaque or other dental material itself is monitored. The other method uses secondary fluorescence, where surfaces in the oral cavity suspected of bearing dental plaque are treated with a fluorescent label material which preferentially binds to dental plaque, and the fluorescence emission of the label material on the oral cavity surfaces to which it has bound is detected to indicate the presence of dental plaque.

In accordance with the foregoing, apparatuses configured for detecting dental plaque sometimes utilizes monochromatic light to illuminate a potential dental plaque site. In certain instances, the site may be illuminated by a light having a predetermined wavelength or range. Other methods and/or apparatuses may utilize a fast excitation pulse (e.g., nanosecond or faster) and fast and sensitive detection devices that are enabled (e.g., gated) at very short time intervals after the excitation pulse. Such methods and/or apparatuses, typically, utilize photomultiplier tubes, avalanche photodiodes and/or Kerr-gates.

While the aforementioned methods and apparatuses are suitable for detecting dental plaque, such methods and apparatuses are generally expensive and include components that are, typically, bulky and require high voltages.

In addition, the aforementioned methods may use one or more calibration methods, e.g., priori knowledge of plaque and background fluorescence lifetimes. For example, one known method uses calibration on a clean enamel site. These methods, however, do not account for variation in background fluorescence within each individual, nor does these methods account for variations in the fluorescence lifetime of different plaque cultures.

SUMMARY

The invention is defined by the independent claims; the dependent claims define advantageous embodiments.

As can be appreciated, a dental apparatus and method of use of the dental apparatus utilizing a modulated excitation signal causing an emitted fluorescence light that is analyzed to detect dental plaque and a calibration module configured to calibrate the dental apparatus for an individual may prove useful in dentistry.

As aspect of the present disclosure provides a dental apparatus. The dental apparatus includes a handle. A controller operably couples to a housing, particularly to the housing provided by the handle, and includes a calibration module configured to calibrate the dental apparatus. The dental apparatus emits a modulated excitation signal and the calibration module compares a detected modulated fluorescence signal with first and second reference values such that if a difference between the detected modulated fluorescence signal and the second reference signal is greater than a difference between the first reference value and the second reference value then the first reference value is updated. A subsystem that is in operable communication with the controller is configured to detect the presence of dental plaque.

A motion sensor may be operably coupled to the dental apparatus and configured to detect a position of the dental apparatus in a mouth of a patient. The calibration module may be configured to shift the first and second reference values per use of the dental apparatus to compensate for changes in one of tooth and dental plaque properties. The calibration module may be configured to store information pertaining to one or more properties associated with teeth of a user. The information pertaining to the teeth of a user may include staining of teeth as a result of age of an individual and dental plaque population of teeth as a result of changing diet. The calibration module may be configured to default to a predetermined first reference value that corresponds to an average value of known users. The controller may include memory for storing a plurality of calibration values one of which may correspond to a clean tooth value for setting the first reference value and one of which may correspond to a tooth covered with dental plaque for setting the second reference value.

The subsystem may be configured to generate an excitation signal causing an emitted fluorescence light to be reflected back to the subsystem and to the controller for analyzing one or more properties of the emitted fluorescence light. The property may correspond to a decay time of the emitted fluorescence light and may be utilized to detect the presence of dental plaque. The excitation signal may be frequency or time modulated and provided on one of a single frequency and multiple frequencies.

The subsystem may include one or more of the following components: a light emitting diode; a laser diode; a filter; a photodetector; an imaging sensor; an amplifier; an oscillator; a mixer; an optical unit (e.g., a beam-splitter); and an analog to digital converter. The filter may be an excitation cleanup filter, the oscillator may be a single or multi-frequency modulated oscillator and the beam-splitter may be a dichroic beam-splitter.

The subsystem may be configured to detect emitted fluorescence light in a frequency that ranges from about 10 Hz to about 10 GHz. A battery may be housed within the handle and is configured to supply power to the dental apparatus including a motor that is housed within the handle and the subsystem, which is housed in a shaft that extends distally from handle. A toothbrush assembly may be configured to releasably couple to the shaft for at least brushing teeth and removing the dental plaque. A window may be positioned on the toothbrush assembly adjacent a plurality of bristles provided thereon and aligns with the subsystem disposed on the shaft such that the excitation signal and the emitted fluorescence light are passable through the window.

The property of the emitted fluorescence light may be a phase shift associated with the emitted fluorescence light and/or amplitude of the emitted fluorescence light. The controller may include one or more control algorithms configured to analyze the phase shift of the emitted fluorescence light and the amplitude of the emitted fluorescence light utilizing one of a time domain and frequency domain analysis methods.

As aspect of the present disclosure provides a dental apparatus. The dental apparatus includes a handle including a shaft extending distally therefrom and a battery and motor housed therein. A toothbrush assembly is configured to removably couple to the shaft. A controller operably couples to the housing and includes a calibration module configured to calibrate the dental apparatus. The calibration module includes memory for storing a plurality of calibration reference values. The dental apparatus emits a modulated excitation signal and the calibration module compares a detected modulated fluorescence signal with first and second reference values such that if a difference between the detected modulated fluorescence signal and the second reference signal is greater than a difference between the first reference value and the second reference value then the first reference value is updated. A subsystem is in operable communication with the controller and configured to detect the presence of dental plaque.

A motion sensor may be operably coupled to the dental apparatus and configured to detect a position of the dental apparatus in a mouth of a patient. The calibration module may be configured to shift the first and second reference values per use of the dental apparatus to compensate for changes in one of tooth and dental plaque properties. The calibration module may be configured to store information pertaining to one or more properties associated with teeth of a user. The information pertaining to the teeth of a user may include staining of teeth as a result of age of an individual and dental plaque population of teeth as a result of changing diet. The calibration module may be configured to default to a predetermined first reference value that corresponds to an average value of known users. The controller may include memory for storing a plurality of calibration values one of which may correspond to a clean tooth value for setting the first reference value and one of which may correspond to a tooth covered with dental plaque for setting the second reference value.

The subsystem may be configured to generate an excitation signal causing an emitted fluorescence light to be reflected back to the subsystem and to the controller for analyzing one or more properties of the emitted fluorescence light. The property may correspond to a decay time of the emitted fluorescence light and may be utilized to detect the presence of dental plaque. The excitation signal may be frequency modulated and provided on one of a single frequency and multiple frequencies.

The subsystem may include one or more of the following components: a light emitting diode; a laser diode; a filter; a photodetector; an imaging sensor; an amplifier; an oscillator; a mixer; an optical unit (e.g., a beam-splitter); and an analog to digital converter. The filter may be an excitation cleanup filter, the oscillator may be a single or multi-frequency modulated oscillator and the beam-splitter may be a dichroic beam-splitter.

The subsystem may be configured to detect emitted fluorescence light in a frequency that ranges from about 10 Hz to about 10 GHz. A battery may be housed within the handle and is configured to supply power to the dental apparatus including a motor that is housed within the handle and the subsystem, which is housed in a shaft that extends distally from handle. A toothbrush assembly may be configured to releasably couple to the shaft for at least brushing teeth and removing the dental plaque. A window may be positioned on the toothbrush assembly adjacent a plurality of bristles provided thereon and aligns with the subsystem disposed on the shaft such that the excitation signal and the emitted fluorescence light are passable through the window.

The property of the emitted fluorescence light may be a phase shift associated with the emitted fluorescence light and/or amplitude of the emitted fluorescence light. The controller may include one or more control algorithms configured to analyze the phase shift of the emitted fluorescence light and the amplitude of the emitted fluorescence light utilizing one of a time domain and frequency domain analysis methods.

An aspect of the instant disclosure provides a method for detecting dental plaque at a site on a tooth. A first modulated excitation calibration signal is emitted from a dental apparatus that is configured to detect the presence of dental plaque. A difference between a detected modulated excitation calibration signal fluorescence and a second reference value is compared with a difference between the second reference signal and a first reference signal such that if the difference between the detected modulated fluorescence signal and the second reference signal is greater than the difference between the first reference value and the second reference value then the first reference value is updated. A second modulated excitation signal is emitted inside a mouth of a patient. An emitted fluorescence light of the second modulated excitation signal is detected. And, one or more properties of the emitted fluorescence light of the second excitation signal are analyzed to detect the presence of dental plaque.

A position of a dental apparatus in a mouth of a patient may be detected via a motion sensor that is operably coupled to the dental apparatus is detected. The first and second reference values may be shifted per use of the dental apparatus to compensate for changes in one of tooth and dental plaque properties. Information pertaining to the property associated with teeth of a user may be stored in a calibration module of the dental apparatus. Information pertaining to staining of teeth as a result of age of an individual and dental plaque population of teeth as a result of changing diet may be stored in the calibration module. A plurality of calibration values one of which corresponding to a clean tooth value for setting the first reference value and one of which corresponding to a tooth covered with dental plaque for setting the second reference value may be stored in the calibration module.

The first and second excitation signals may be frequency or time modulated on a single frequency and/or multiple frequencies. The emitted fluorescence light of the second excitation signal may be detected in a frequency that ranges from about 10 Hz to about 10 GHz. A phase shift and/or amplitude of the emitted fluorescence light may be analyzed. One of time domain and frequency domain analysis methods may be utilized to analyze the phase shift and amplitude of the emitted fluorescence light.

The dental apparatus may be provided with a handle including a battery that is configured to supply power to the dental apparatus including a motor that is housed within the handle, a controller and subsystem, which is housed in a shaft that extends distally from handle. The subsystem may be provided with one or more of the following components: a light emitting diode; a laser diode; a filter; a photodetector; an imaging sensor; an amplifier; an oscillator; a mixer; an optical unit (e.g., a beam-splitter); and an analog to digital converter. The filter may be an excitation cleanup filter, the oscillator may be a single or multi-frequency modulated oscillator and the beam-splitter may be a dichroic beam-splitter. A toothbrush assembly may be configured to releasably couple to the shaft for at least brushing teeth and removing the dental plaque. The dental apparatus may be provided with a window that is positioned on the toothbrush assembly adjacent a plurality of bristles provided thereon and may align with the subsystem disposed on the shaft such that the excitation signal and the emitted fluorescence light are passable through the window.

BRIEF DESCRIPTION OF THE DRAWINGS

The aspects of the present disclosure may be better understood with reference to the following figures. The components in the figures are not necessarily to scale, emphasis instead being placed upon clearly illustrating the principles of the disclosure. Moreover, in the figures, like reference numerals designate corresponding parts throughout the several views.

In the figures.

DETAILED DESCRIPTION OF EMBODIMENTS

The present disclosure describes various embodiments of apparatuses and methods that utilize one or more power levels of excitation light for detecting one or more tooth anomalies such that the tooth anomalies may be removed. Specifically, a dental apparatus, e.g. an electric toothbrush, is configured to provide a modulated excitation light that is configured to cause an emitted fluorescence light to be reflected back to the dental apparatus for analyzing one or more parameters of the emitted fluorescence that correspond to a decay time of the emitted fluorescence light. The modulated excitation signal may be frequency modulated or time modulated (e.g., pulse excitation) The one or more parameters are, subsequently, utilized to detect the presence of a tooth anomaly, e.g., dental plaque. When the dental plaque is detected, the dental apparatus may then be utilized to remove the dental plaque. Moreover, the dental apparatus is configured to automatically calibrate during use thereof without any manual input from the user.

Figure 1A:
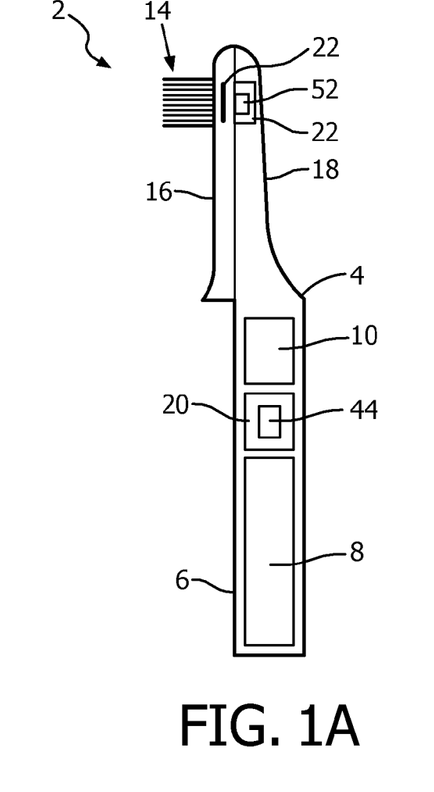
FIGS. 1A and 1B are side and front views, respectively, of a dental apparatus according to an embodiment of the instant disclosure.
Figure 1B:
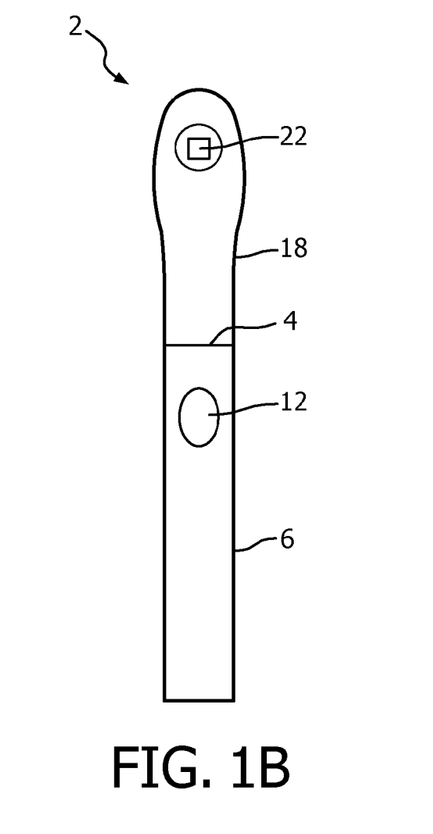

FIG. 1A illustrates a system 2 that is configured to detect dental plaque. System 2 may be configured for use with a variety of handheld dental implements. In the illustrated embodiment, system 2 is in the form of a multipurpose dental apparatus 4 (e.g., a combination electric toothbrush and dental plaque detector). Dental apparatus 4 includes a handle 6 of suitable configuration that is configured to house a battery 8 and an electric motor 10. A power button or switch 12 (FIG. 1B) is provided on the handle 6 and operably couples to battery 8 for supplying power to dental apparatus 4 and components operably associated therewith, e.g., electric motor 10, a controller 20, etc., when depressed. A plurality of bristles 14 of suitable configuration is provided on toothbrush assembly 16 that is configured to detachably couple via one or more coupling methods, e.g., clips (not explicitly shown), to a shaft 18 that extends distally from handle 6.

Figure 2:
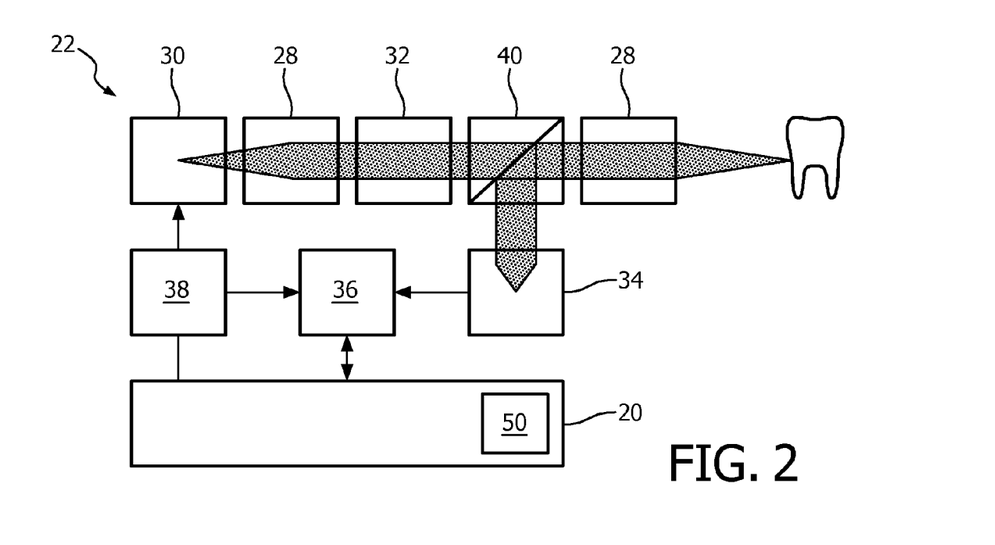
FIG. 2 is a block diagram illustrating a controller and subsystem of the dental apparatus.

FIG. 2 is block diagram illustrating an embodiment of a controller 20 and subsystem 22 that may be provided with dental apparatus 4. Subsystem 22 may include any suitable electrical and/or non-electrical components that are capable of generating, emitting and/or detecting various power intensities and wavelengths of frequency modulated excitation light, e.g. blue light, red light etc. Subsystem 22 may include, without limitation, for example, one or more light sources 30, photodetectors 34, lock-in amplifier 36, oscillators 38, optical units (e.g., a beam splitter 40), and optical components 28.

Light sources 30 may be any suitable light source. In the embodiment illustrated in FIG. 2, light source 30 is in the form of one or more light emitting diodes 30, e.g., a plurality of light emitting diodes 30 (LEDs 30). LEDs 30 may be configured to generate or emit one or more suitable wavelengths of light. In accordance with the instant disclosure, for example, it is has been found that light having wavelengths of 405 nm, 440 nm, 470 nm and/or 480 nm (all visible light, e.g., blue light) were suitable for the purposes described herein. Specifically, light in the visible light spectrum was chosen due to the safety concerns of using other wavelengths of light, e.g., ultraviolet light, infrared, etc., in the mouth, and the cost typically attributed with utilizing such wavelengths of light. Other light sources, e.g. diode laser, and different wavelengths may also be utilized.

Photodetectors 34 are configured to detect the presence of dental plaque on tooth enamel. Specifically, photodetectors 34 are configured and utilized to detect emitted fluorescence associated with tooth material and/or with dental plaque and convert detected emitted fluorescence photons into an electrical signal that is sent to a controller 20 for processing, described in greater detail below.

In accordance with the instant disclosure, photodetectors 34 may be configured to detect emitted fluorescence associated with tooth material and/or with dental plaque in a frequency that ranges from about 10 Hz to about 10 GHz. In one particular embodiment, for example, the frequency may range from about 1 MHz to about 10 GHz. In another embodiment, the frequency may range from about 10 Hz to about 100 MHz; this particular embodiment may be utilized to optimize signal to noise related to emitted fluorescence decay characteristics of tooth material. Alternatively, in embodiments, image sensors (not explicitly shown) may be utilized in place of photodetectors 34. In this particular embodiment, image processing may be utilized to convert pixel intensities into a form that can be used to determine when dental plaque has been detected. While photodetectors 34 and the image sensors are both suitable for detecting the aforementioned emitted fluorescence associated with tooth material and/or dental plaque, the simplicity of photodetectors 34 makes them ideal for the purposes described herein. As can be appreciated, dental apparatus 4 may include a combination of photodetectors 34 and imaging sensors.

In order to shield photodetectors 34 from various wavelengths of excitation light and/or unwanted background radiation, optical filters (not explicitly shown) may be mounted onto photodetectors 34. Additionally, photodetectors 34 may include one or more collection and focusing optics such as, for example, lenses, compound parabolic concentrators or a combination of both.

The optical unit may be configured to remove reflected excitation light and/or receiving fluorescence light beam from teeth. With this purpose in mind, beam-splitter 40 is utilized to direct frequency modulated excitation light towards teeth and reflect the emitted fluorescence light, which has a longer wavelength, towards photodetectors 34. Accordingly, a dichroic beam splitter which has a short-pass characteristic was utilized for this purpose. Alternatively, instead of using beam splitter 40, two optical paths, one for excitation and one for detection may be utilized; this may be advantageous in certain embodiments, e.g., to accommodate design variations of dental apparatus 4. As can be appreciated, other suitable optical units may also be utilized to provide the functions associated with beam splitter 40.

An optional filter 32 may be provided and utilized to block any undesired wavelengths (e.g. ultraviolet light) of light from reaching the teeth or the photodetectors 34. In the illustrated embodiments, for example, filter 32 is an excitation cleanup filter, e.g., a narrow bandpass filter. Filter 32 may be arranged in other configurations to accommodate different wavelengths and/or power intensities of light and/or to achieve different filtering outcomes.

Oscillator 38 may be any suitable oscillator. In the illustrated embodiment, oscillator 38 is operably coupled to LEDs 30 and configured to drive LEDs 30 such that LEDs 30 generate or emit a frequency modulated excitation light or signal. The frequency modulated excitation signal may be emitted at a single frequency or multi-frequencies simultaneously; the latter may be implemented as multiple discrete frequencies (or mixed together) and used to discriminate against potentially interfering materials in a mouth of a user, e.g., composite fillings.

Lock-in amplifier 36 is configured to receive input signals from oscillator 38 and photodetectors 34 and outputs a corresponding signal that corresponds to the detected emitted fluorescence to controller 20. Specifically, oscillator 38 provides a reference frequency (e.g., the frequency of the frequency modulated excitation signal) to lock-in amplifier 36. Lock-in amplifier 36 utilizes this reference frequency to filter out the unwanted portions, e.g., noise, of the signal received from photodetectors 34 and communicates the remaining portions of the signal that is required for processing to controller 20. In essence, lock-in amplifier 36 functions as a phase sensitive detector. As can be appreciated, other amplifiers and/or signal processing devices may be utilized for the purposes described herein.

Subsystem 22 is configured to illuminate tooth material (and in some instances gums) from the frequency modulate excitation signal emitted through toothbrush assembly 16 adjacent to where plurality of bristles 14 are disposed. With this purpose in mind, an optical window 24 (FIGS. 1A and 1B) of suitable of configuration is provided on toothbrush assembly 16 adjacent plurality of bristles 14 and is configured to allow light to pass therethrough for detection thereof by subsystem 22. Specifically, when toothbrush assembly 16 is coupled to shaft 18, window 24 aligns with subsystem 22 including LEDs 30, photodetectors 34, amplifiers 36, oscillators 38, beam splitters 40, and optical components 28 such that the frequency modulated excitation signal generated from LEDs 30 is emitted through window 24 and reflected light (e.g., emitted fluorescence of tooth material and/or dental plaque) is transmitted back through window 24 and detected by photodetectors 34.

With reference again to FIG. 1A, dental apparatus 4 includes controller 20 (e.g., a microprocessor) that communicates with subsystem 22 (as best seen in FIG. 2) that is configured to generate, emit and detect light, e.g., frequency modulated excitation signal and emitted fluorescence associated with tooth material and dental plaque. Controller 20 can be a processor, microcontroller, a system on chip (SOC), field programmable gate array (FPGA), etc. Collectively the one or more components, which can include a processor, microcontroller, SOC, and/or FPGA, for performing the various functions and operations described herein are part of a controller 20, as recited, for example, in the claims. Controller 20 can be provided as a single integrated circuit (IC) chip which can be mounted on a single printed circuit board (PCB). Alternatively, the various circuit components of controller 20, including, for example, the processor, microcontroller, etc. are provided as one or more integrated circuit chips. That is, the various circuit components may be located on one or more integrated circuit chips.

Controller 20 communicates with subsystem 22 and is configured to analyze one or more properties of the emitted fluorescence light. In the illustrated embodiment, the one or more properties of the emitted fluorescence light may be phase shift associated with the emitted fluorescence light and/or amplitude of the emitted fluorescence light.

In accordance with the instant disclosure, the phase shift (and/or amplitude) is correlated to a decay time of the emitted fluorescence light and utilized to detect the presence of dental plaque. Specifically, through empirical testing it has been found that there is a direct correlation between a phase shift (and/or amplitude) of detected emitted fluorescence light and fluorescence decay times. More specifically, it is known that emitted fluorescence from a tooth without dental plaque on a surface thereof decays more slowly when compared to emitted fluorescence from a tooth with dental plaque, i.e., a tooth with dental plaque decays faster. Accordingly, detected emitted fluorescence of a tooth with dental plaque will have a lower phase shift at a specific frequency range when compared to a phase shift of detected fluorescence of a tooth without dental plaque. At low frequencies, for example, the phase shift will be zero for both cases, e.g., tooth with/without dental plaque. At very high frequencies both situations will show 90 degrees of phase shift. At frequencies between these two extremes, the phase shift of clean enamel/dentine will be greater than that of the enamel/dentine covered with plaque. In other words: A faster decay time (time domain) means a lower phase shift in the frequency domain. A similar correlation can be made with respect to amplitude demodulation: the demodulation of the fluorescence light of a clean enamel/dentin site will be greater at a specific modulation frequency than the demodulation of the fluorescence light of the same site covered with dental plaque. If we analyze the detected fluorescence response in the time-domain (i.e. in the case of pulse excitation), the observed fluorescence intensity at a specific time after excitation would be greater for a clean enamel/dentine site than that of the enamel/dentine covered with plaque. In accordance with the foregoing, controller 20 includes one or more control algorithms that are configured to analyze a phase shift (and/or amplitude) of the emitted fluorescence light utilizing time domain and/or frequency domain analysis methods. The control algorithm may utilize one or more transforms to calculate the phase shift (and/or amplitude). For example, Discrete Fourier Transform (DFT), Fast Fourier Transform (FFT) and/or Laplace Transform may be utilized to calculate the phase shift and/or amplitude of the detected emitted fluorescence.

As is known, there is a certain variation in lifetime decay data of human enamel. Although the aforementioned dental apparatus 4 does not rely on the determination of the actual decay-times, variations of actual decay-times may limit an effective signal range that may be utilized by controller 20; thus limiting the detection of low levels of plaque coverage as a result of variability in tooth enamel between individuals.

Figure 4:
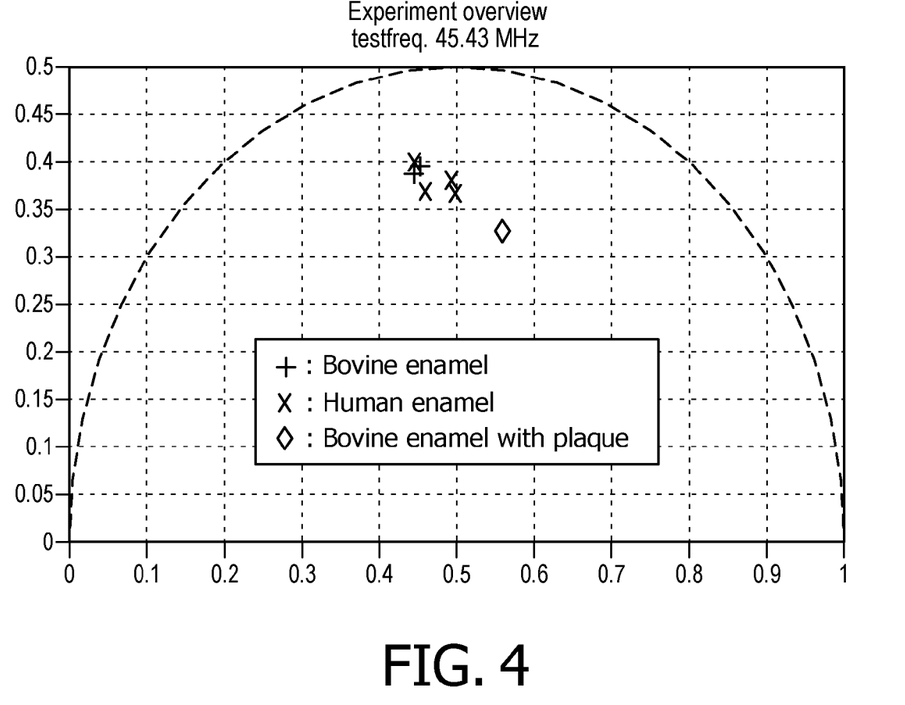
FIG. 4 is a graph of measurements taken from different samples of teeth illustrating variability of tooth enamel associated with the different samples.

For example, FIG. 4 shows a polar plot of tooth enamel from different samples, e.g., bovine tooth enamel, human tooth enamel and bovine enamel covered with dental plaque. Specifically, a detected fluorescence is plotted as M sin ($\Phi$) versus M cos ($\Phi$) (e.g., the 90° phase shifted component vs. in-phase part of the response). In FIG. 4, clean dentine is described as a locus starting near [1:0] at low frequencies and progressing towards the origin for higher frequencies. In accordance with the instant disclosure, a phase angle which is an angle between the x-axis and the location at a given frequency and the distance from the origin provides for a magnitude of the response.

As is evident from FIG. 4, there is a scatter in a location of the clean tooth signal. As can be appreciated, variability in a dental plaque signal is expected due to the varying composition of dental plaque between individuals, due to, for example, their different diet, oral hygiene habits, genetics, etc. This variation, however, in a signal corresponding to a clean tooth and signal corresponding to a tooth covered with dental plaque is a variation between individuals and is detectable and/or removed by a calibration step that is performed from controller 20.

Specifically, controller 20 is configured to emit a calibration excitation signal on a clean piece of tooth material for each individual user. To this end, a calibration module 44 (FIG. 1A) may be in operable communication with controller 20 and configured to calibrate dental apparatus 4; as can be appreciated, this may maximize an effective signal range that may utilized by controller 20. Specifically, by calibrating out all phase delays and frequency dependent gains on a clean tooth, the aforementioned analysis will provide a more accurate measure of the amount of dental plaque detected and, thus, maximize dental plaque detection and/or removal.

Figure 5:
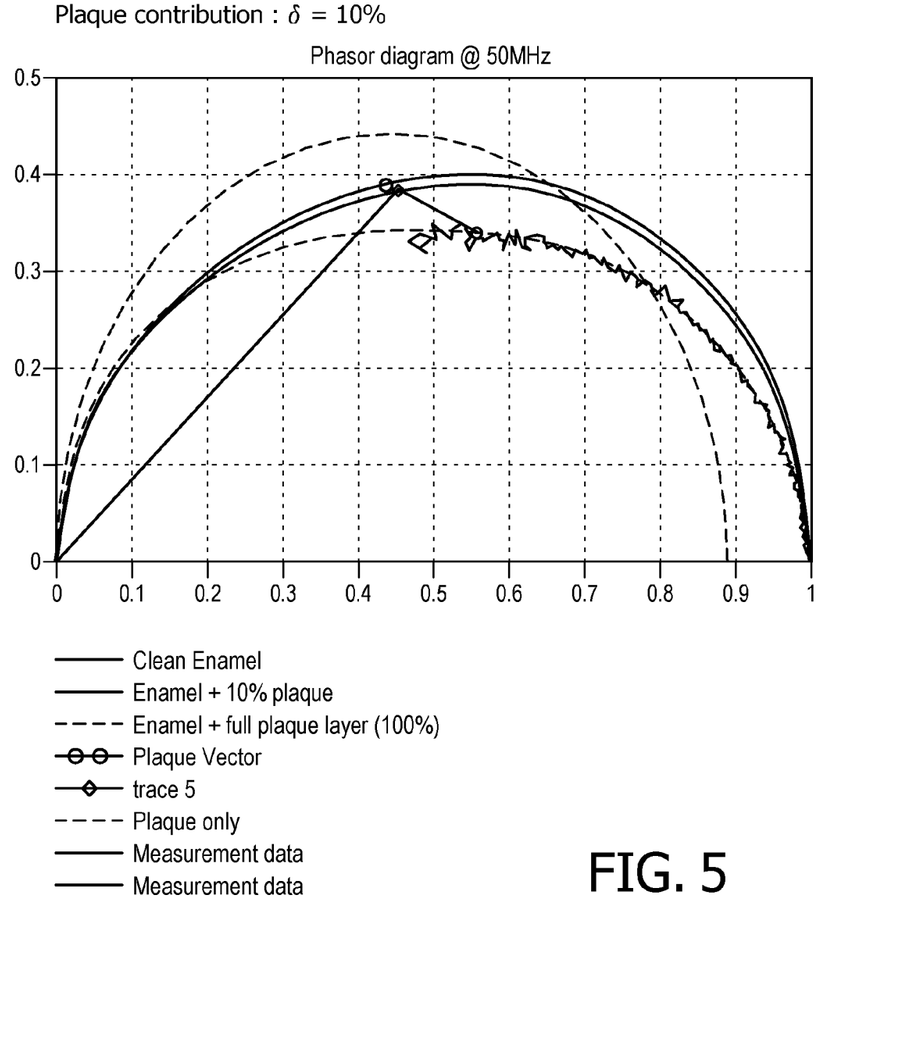
FIG. 5 is a polar diagram of a signal corresponding to a clean tooth vs. a signal corresponding to a tooth covered with dental plaque.

In accordance with the instant disclosure, data relating to a signal corresponding to a clean tooth (e.g., a first reference signal) and a signal corresponding to a tooth covered with dental plaque (e.g., a second reference signal) was plotted as a polar diagram to illustrate a difference in these signals at a particular frequency (FIG. 5). The polar diagram shows a tooth with full plaque coverage and a tooth with no plaque, i.e., a tooth with a clean surface, and allows a prediction of were a tooth with partial plaque coverage may lie on a line along the plaque vector; with low dental plaque coverage being near the clean tooth location. Thus, a measure of the degree of dental plaque coverage is possible, provided the end points of the vector are known.

Dental apparatus 4 is configured to emit a frequency modulated excitation calibration signal during brushing. Specifically, calibration module 44 performs a calibration step that utilizes one or more data look-up tables 50 that include the signals from a clean tooth (e.g., the first reference signal) and a tooth covered in plaque (e.g., the second reference signal) from polar diagram of FIG. 5, and uses this information for preliminary feedback. Data look-up tables 50 may be in the form of non-volatile updatable memory to store the signals from a clean tooth and a tooth covered in plaque obtained from the above referenced polar diagram as calibration values. As can be appreciated, the polar diagram in FIG. 5 and/or the measurements taken from FIG. 4 may vary as a result of the specific samples of teeth that are utilized.

During brushing, calibration module 44 compares a detected frequency modulated fluorescence signal with the first and second reference values. Specifically, if a difference between the detected frequency modulated fluorescence signal and the second reference signal (e.g., a most extreme plaque-like value towards the lower right portion of FIG. 4) is greater than a difference between the first reference value (e.g., a most extreme tooth-like value towards the upper left portion of FIG. 4) and the second reference value then the first reference value is updated. In one particular embodiment, the first reference signal may be updated to a value that is close or equal to the detected frequency modulated fluorescence signal. This auto calibration process enables calibration module 44 to detect lower levels of plaque coverage when compared to conventional dental plaque detectors and maintain useful feedback information.

In accordance with the instant disclosure, raw data, e.g., calibration values for "n" number of potential users, is stored in data look-up table(s) 50 and may be measured at multiple frequencies, to enable better separation of a clean tooth from a tooth covered with dental plaque. In this instance, the calibration may be calculated separately for each frequency, or it may be calculated in a linked way by fitting to a decay model for each extreme state.

If dental apparatus 4 is utilized or shared by multiple users, calibration module 44 may be configured to detect different toothbrush assemblies 14. In this instance, for example, one or more mechanical and/or electrical devices may be provided on dental apparatus 4 and in operable communication with calibration module 4. In the event of multiple users being detected by calibration module 44, clean tooth and dental plaque covered tooth calibration values may be stored for each user, and the stored values may be used (and further updated if appropriate) per user. When a new user is detected, calibration module 44 may default to predetermined value, or an average value of the known users.

Moreover, calibration values may be automatically shifted along the dental plaque covered tooth vector towards the opposite state, e.g., clean tooth vector, by a predetermined amount for each usage. As can be appreciated, this would help calibration module 44 compensate for gradual changes in the clean tooth and/or dental plaque covered tooth properties. The gradual changes may include, for example, gradual staining of a user's teeth through age and/or drift of dental plaque population due to a changing diet.

In embodiments, an optional motion sensor 52 (FIG. 1A for example) may be provided in subsystem 22 and utilized to detect an approximate position within a mouth of a user. In this embodiment, sensor 52 may be utilized to allow calibration module 44 to compensate for different positions within a user's mouth, should there be a significant variation inside the mouth.

Operation of system 2 is described in terms of a method 100 for detecting dental plaque. Dental apparatus 4 may, initially, be positioned within a mouth of a user. When the dental apparatus 4 is powered on, calibration module 44 may be configured to automatically calibrate dental apparatus 4 (see FIG. 6 at step 102); this calibration of dental apparatus 4 is essentially transparent to a user in that a user is unaware of the calibration step being performed. Specifically, a frequency modulated excitation calibration signal is emitted from LEDs 30 and detected from photodetectors 34, which, in turn, communicates the detected calibration signal fluorescence light to calibration module 44 for processing thereof. In the illustrated embodiment, calibration module 44, initially, compares the detected calibration signal with a known reference value for a clean tooth complied in the data look-up tables 50. In this instance, the known reference value corresponds to the upper left portion of FIG. 4 and is used to detect high levels of dental plaque.

Figure 6:
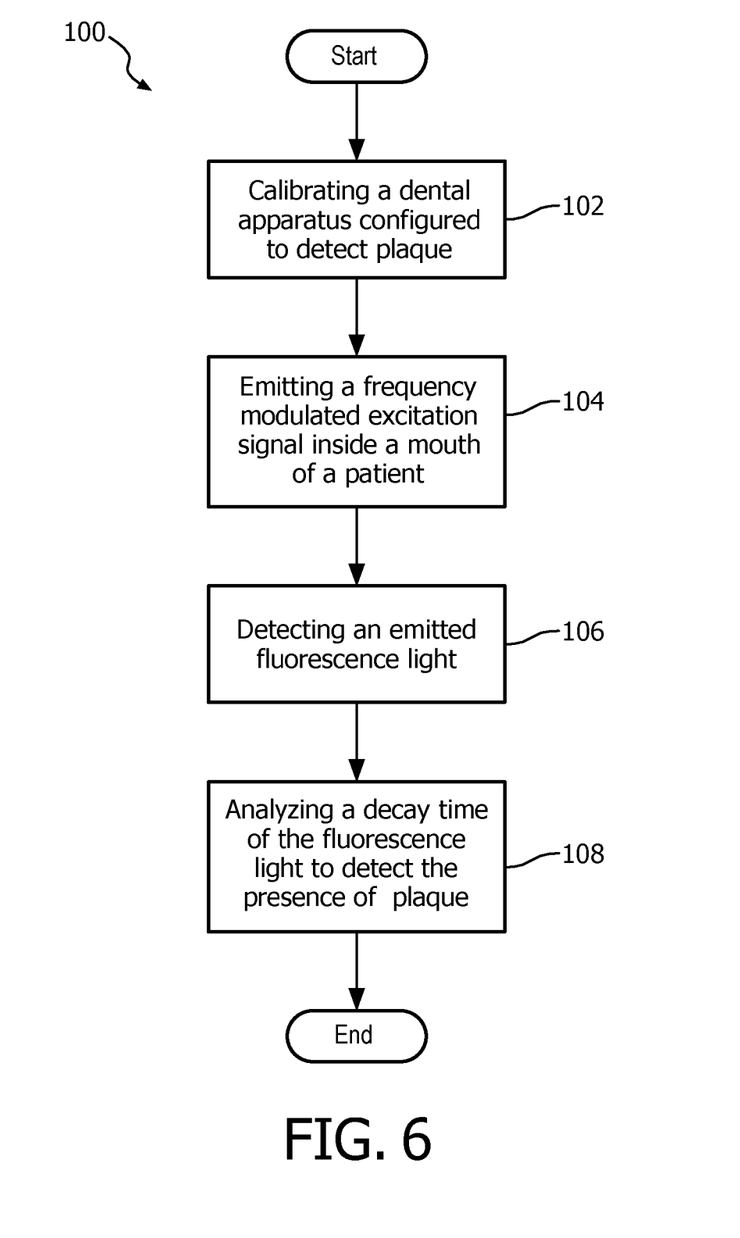
FIG. 6 is a flow chart illustrating a method of detecting dental plaque.

Thereafter, plurality of bristles 14 are activated and rotated, in conventional fashion, and a frequency modulated excitation signal is emitted from LEDs 30 (see FIG. 6 at step 104) which causes an emitted fluorescence light to be reflected back to photodetectors 34 (see FIG. 6 at step 106).

Then, controller 20 receives an output signal from lock-in amplifier 36. The control algorithm utilizes one or more of the aforementioned transforms to calculate the phase shift (and/or amplitude) of the detected emitted fluorescence (see FIG. 6 at step 108). Controller 20 utilizes a closed loop feedback loop to continuously monitor the presence of a phase shift of the detected emitted fluorescence to ensure that all dental plaque is removed from a tooth site. In embodiments, dental apparatus 4 may be equipped with one or more indicating devices, e.g., audio, visual, etc. (not explicitly shown), that are configured to give a user an indication when a specific site on the tooth is clean. After such an indication, a user can then move to a different site on the tooth or the next tooth. As can be appreciated, this may reduce the overall brushing time of user and/or may also lead to a better, more conscious brushing routine.

The aforementioned process repeats to continuously measure a level of dental plaque on the current tooth being brushed. Dental apparatus 4 can communicate the presence of dental plaque to the user in a wide variety of ways e.g. by illuminating one more LEDS on handle 8 (not explicitly shown).

Dental apparatus 4 helps a user clean their teeth while informing the user if they are removing dental plaque from their teeth and if they have fully removed the dental plaque. Moreover, dental apparatus 4 provides information regarding dental plaque in real time during brushing. Dental apparatus 4 accomplishes the foregoing, without the use of the aforementioned bulky, expensive components that utilize high voltage and that are typically associated with convention dental plaque apparatuses.

From the foregoing and with reference to the various figure drawings, those skilled in the art will appreciate that certain modifications can also be made to the present disclosure without departing from the scope of the same. For example, in some embodiments, electrical circuitry 22 may be built into handle 8 to allow shaft 18 to be replaced. In this instance, frequency modulated excitation signals may be delivered to toothbrush assembly 16 and emitted fluorescence light reflected back to photodetectors 34 and controller 20 via optical fibers (not explicitly shown). Moreover, in this embodiment, one or more light guides (not explicitly shown) may be provided on dental apparatus 4 and configured to channel light to and from window 24.

In the embodiment illustrated in FIG. 2, controller 20 and electrical circuitry 22 are configured to function in an analogue domain. In embodiments (see FIG. 3 for example), however, oscillator 38 and/or lock-in amplifier 36 can be implemented in a digital domain. In this particular embodiment, digital implementation may be included into controller 20, e.g., an analog heterodyning stage, to down convert signals to an intermediate frequency band better suited for analog-to-digital conversion. Specifically, for each frequency modulated excitation signal, oscillator 38 (a digital oscillator for example) generates a frequency modulated excitation signal with a small offset for a mixer 42 that outputs fall in a frequency range of an analog-to-digital converter 46. Thereafter, all remaining signal processing is done digitally and in accordance with the above.

Figure 3:
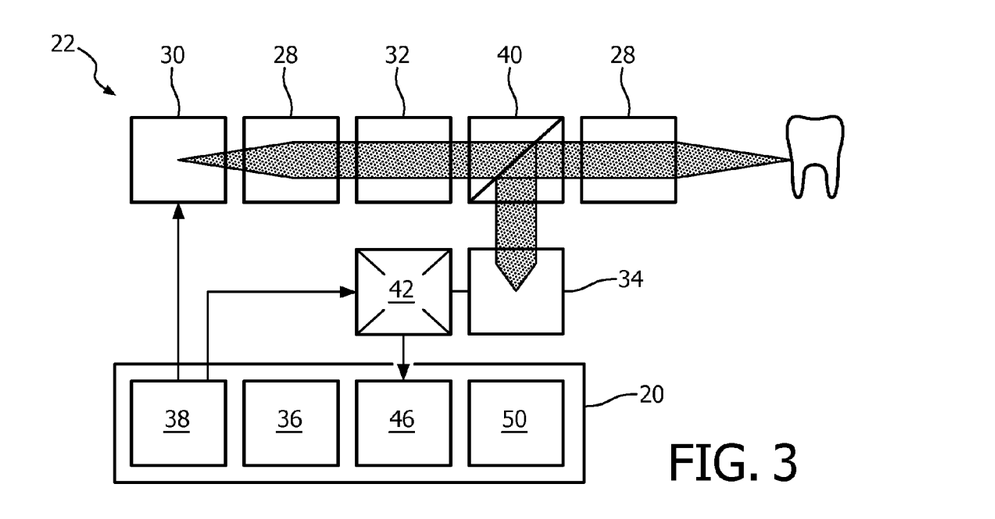
FIG. 3 is a block diagram illustrating a controller and subsystem of the dental apparatus according to another embodiment of the instant disclosure.

Moreover, in the instance where a large number of fluorescence measurements are needed, oscillator 38 and LEDs 30 may be configured to generate and emit a maximum length sequence, which would allow detection of fluorescence over a large number of frequencies simultaneously. In this instance, controller 20 may include one or more analogue to digital converters 46 and a suitable digital processing unit (not explicitly shown) configured to extract the separate frequency responses and/or transform the separate frequency responses into an impulse response.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

The invention claimed is:

1. A dental apparatus, comprising:
a handle; including a shaft extending distally therefrom and a battery and motor housed therein;
a toothbrush assembly configured to removably couple to the shaft;
a controller operably coupled to the housing that includes a calibration module configured to calibrate the dental apparatus, wherein the dental apparatus emits a modulated excitation signal and the calibration module compares a detected modulated fluorescence signal with first and second reference values such that if a difference between the detected modulated fluorescence signal and the second reference signal is greater than a difference between the first reference value and the second reference value then the first reference value is updated; and
a subsystem that is in operable communication with the controller and configured to detect the presence of dental plaque.

2. The dental apparatus according to claim 1, wherein a motion sensor is operably coupled to the dental apparatus and configured to detect a position of the dental apparatus in a mouth of a patient.

3. The dental apparatus according to claim 1, wherein the calibration module is configured to shift the first and second reference values per use of the dental apparatus to compensate for changes in one of tooth and dental plaque properties.

4. The dental apparatus according to claim 1, wherein the calibration module is configured to store information pertaining to at least one property associated with teeth of a user.

5. The dental apparatus according to claim 1, wherein the controller includes memory for storing a plurality of calibration values at least one of which corresponding to a clean tooth value for setting the first reference value and at least one of which corresponding to a tooth covered with dental plaque for setting the second reference value.

6. The dental apparatus according to claim 1, wherein the subsystem is configured to generate an excitation signal causing an emitted fluorescence light to be reflected back to the subsystem and to the controller for analyzing at least one property of the emitted fluorescence light, the at least one property corresponding to a decay time of the emitted fluorescence light and utilized to detect the presence of dental plaque.

7. The dental apparatus according to claim 1, wherein the subsystem is configured to detect emitted fluorescence light in a frequency that ranges from about 10 Hz to about 10 GHz.

8. The dental apparatus according to claim 1, wherein a window is positioned on the toothbrush assembly adjacent a plurality of bristles provided thereon and aligns with the subsystem disposed on the shaft such that the excitation signal and the emitted fluorescence light are passable through the window.

9. A method for detecting dental plaque at a site on a tooth, comprising:
   emitting a first modulated excitation calibration signal from a dental apparatus configured to detect the presence of dental plaque;
   comparing a difference between a detected modulated excitation calibration signal fluorescence and a second reference value with a difference between the second reference signal and a first reference signal such that if the difference between the detected modulated fluorescence signal and the second reference signal is greater than the difference between the first reference value and the second reference value then the first reference value is updated;
   emitting a second modulated excitation signal inside a mouth of a patient;
   detecting an emitted fluorescence light of the second modulated excitation signal; and
   analyzing at least one property of the emitted fluorescence light of the second excitation signal to detect the presence of dental plaque.

10. The method according to claim 9, including storing information pertaining to at least one property associated with teeth of a user in a calibration module of the dental apparatus.

11. The method according to claim 9, including storing into memory a plurality of calibration values at least one of which corresponding to a clean tooth value for setting the first reference value and at least one of which corresponding to a tooth covered with dental plaque for setting the second reference value.

12. The method according to claim 9 including one of frequency modulating and time modulating the first and second excitation signals on one of a single frequency and multiple frequencies.

13. The method according to claim 12 wherein analyzing includes analyzing one of a phase shift and amplitude of the emitted fluorescence light.

14. The method according to claim 13, including utilizing at least one of time domain and frequency domain analysis methods to analyze the phase shift and amplitude of the emitted fluorescence light.

15. The method according to claim 9, including detecting the emitted fluorescence light of the second excitation signal in a frequency that ranges from about 10 Hz to about 10 GHz.

* * * * *